United States Patent [19]

French et al.

[11] Patent Number: 4,844,072
[45] Date of Patent: Jul. 4, 1989

[54] LIQUID-CIRCULATING THERMAL THERAPY SYSTEM

[75] Inventors: Ronald L. French, Villa Hills, Ky.; Ronald E. Smith, Hamilton; Mark J. Buch, Cincinnati, both of Ohio

[73] Assignee: Seabrook Medical Systems, Inc., Cincinnati, Ohio

[21] Appl. No.: 814,220

[22] Filed: Dec. 27, 1985

[51] Int. Cl.$^4$ ............................ A61F 7/00; H05B 1/02
[52] U.S. Cl. ...................................... 128/400; 219/297; 219/490; 604/291; 324/105; 324/130
[58] Field of Search ............... 128/400; 219/297, 324, 219/322, 490; 604/291, 304; 324/105, 130

[56] References Cited

U.S. PATENT DOCUMENTS

| | | |
|---|---|---|
| 1,896,953 | 2/1933 | Hassell . |
| 2,110,022 | 3/1938 | Kliesrath . |
| 2,198,989 | 4/1940 | Cooley . |
| 2,250,325 | 7/1941 | Barnes . |
| 2,397,232 | 3/1946 | Barnes et al. . |
| 2,726,658 | 12/1955 | Chessey . |
| 2,753,435 | 7/1956 | Jepson . |
| 2,802,088 | 8/1957 | MacCracken . |
| 2,866,072 | 12/1958 | Smith . |
| 2,885,189 | 5/1959 | MacCracken . |
| 2,930,594 | 3/1960 | MacCracken . |
| 2,978,225 | 4/1961 | Dallas, Jr. . |
| 2,982,841 | 5/1961 | MacCracken . |
| 3,092,112 | 6/1963 | Zelony . |
| 3,112,792 | 12/1963 | Coleman, Jr. et al. . |
| 3,211,216 | 10/1965 | Coleman, Jr. et al. . |
| 3,233,662 | 2/1966 | Yat Chuen Yuen . |
| 3,468,311 | 9/1969 | Gallagher . |
| 3,674,034 | 7/1972 | Hardy . |
| 3,714,947 | 2/1973 | Hardy . |
| 3,830,676 | 8/1974 | Elkins . |
| 3,846,615 | 11/1974 | Athey et al. .......................... 219/322 |
| 3,867,939 | 2/1975 | Moore et al. . |
| 3,871,381 | 3/1975 | Roslonski . |
| 3,894,213 | 7/1975 | Agarwala . |
| 3,960,145 | 6/1976 | Scarbrough . |
| 3,967,627 | 7/1976 | Brown . |
| 4,026,299 | 5/1977 | Sauder . |
| 4,098,279 | 7/1978 | Golden . |
| 4,108,146 | 8/1978 | Golden . |
| 4,114,620 | 9/1978 | Moore et al. . |
| 4,118,946 | 10/1978 | Tubin . |
| 4,149,541 | 4/1979 | Gammons et al. . |
| 4,154,245 | 5/1979 | Daily . |
| 4,167,663 | 9/1979 | Granzow, Jr. . |
| 4,170,998 | 10/1979 | Sauder . |
| 4,179,745 | 12/1979 | Wuertele ............................. 324/105 |
| 4,267,611 | 5/1981 | Agulnick . |
| 4,338,944 | 7/1982 | Arkans . |
| 4,459,468 | 7/1984 | Bailey ................................. 128/400 |
| 4,613,746 | 9/1986 | MacLaughlin ...................... 219/490 |
| 4,663,586 | 5/1987 | Swerlein et al. .................... 324/130 |

OTHER PUBLICATIONS

Brochure No. 1181 Cincinnati Sub–Zero Products Inc. Blanketrol ® Hyper–Hypothermia System.

(List continued on next page.)

Primary Examiner—MaryAnn Lastova
Attorney, Agent, or Firm—Frost & Jacobs

[57] ABSTRACT

A system for circulating hot or cold liquid through a pad placed in thermal contact with a patient for thermal therapy. The system includes a flexible thermal pad with an internal channel for carrying the liquid and a pump assembly for circulating and optionally heating the liquid. The patient-contacting surface of the pad comprises a foam having a cushioned surface to reduce the risk of ischemia and enhance patient comfort. An open-cell foam structure absorbs and retains moisture for applying moist heat. The system is microprocessor controlled and includes a heater to warm the liquid to a selectable temperature for heat therapy. A display selectively indicates set-point or actual liquid temperature in either °F. or °C. as desired. Safety features include three separate over-temperature sensors, a tilt switch and a float switch which de-energize both the heater and the pump when an abnormal temperature is sensed, the unit is tipped or a low liquid level is sensed, respectively. A sealed membrane switch assembly protects the unit from spills and includes a concealed set-point switch to prevent unauthorized tampering. Set-point may be decremented to a "heater off" position to permit the circulation of unheated liquid. The temperature controller automatically recalibrates itself periodically.

21 Claims, 8 Drawing Sheets

OTHER PUBLICATIONS

Brochure No. 883 Cincinnati Sub-Zero Products Inc. Blanketrol® II Hyper-Hypothermia System.
Blanketrol® II Operation and Technical Manual, Cincinnati Sub-Zero Products Inc.
Brochure No. 785 Cincinnati Sub-Zero Products Inc. Hemotherm® Dual Reservoir Cooler/Heater.
Hemotherm® Dual Reservoir Cooler Heater Model 400M Operation and Technical Manual.
Brochure No. 483 Cincinnati Sub-Zero Products Inc. Blanketrol® II Hyper-Hypothermia System.
Brochure AG-105-3 American Hamilton Div. of American Hospital Supply-Model K-20 Module.
Brochure AT 1206 American Medical Systems Div. of American Hospital Supply -K-20 Aquamatic K-Module.
Brochure from Gaymar Industries Inc. © 1980 Medi-Therm® Hyper-Hypothermia System.
Advertisement for Gaymar Industries Inc. MUL-T-PAD ™ and T/PUMP ™.
Advertisement for Gaymar Industries Inc. MUL-T-PAD ™ and T/PUMP ™.
Brochure on MUL-T-PAD and T/PUMP Gaymar Industries Inc.
Brochure AT 1207–American Medical Systems Div. of American Hospital Supply Corp. Model RK-300 Hypo/Hypothermia System.
Brochure AT 1208 showing American Medical Systems Div. of American Hospital Supply Corp. Model RK-600 Hypo/Hyperthermia System.
Brochure AT 1209 showing American Medical Systems Div. of American Hospital Supply Corp. Model RK-1000 Hypo/Hyperthermia System.
Williams, Earl, *A Thermoelement Comparator for Automatic AC-DC Difference Measurements*, IEEE vol. IM-29, No. 4, Dec. 1980, pp. 405-409.

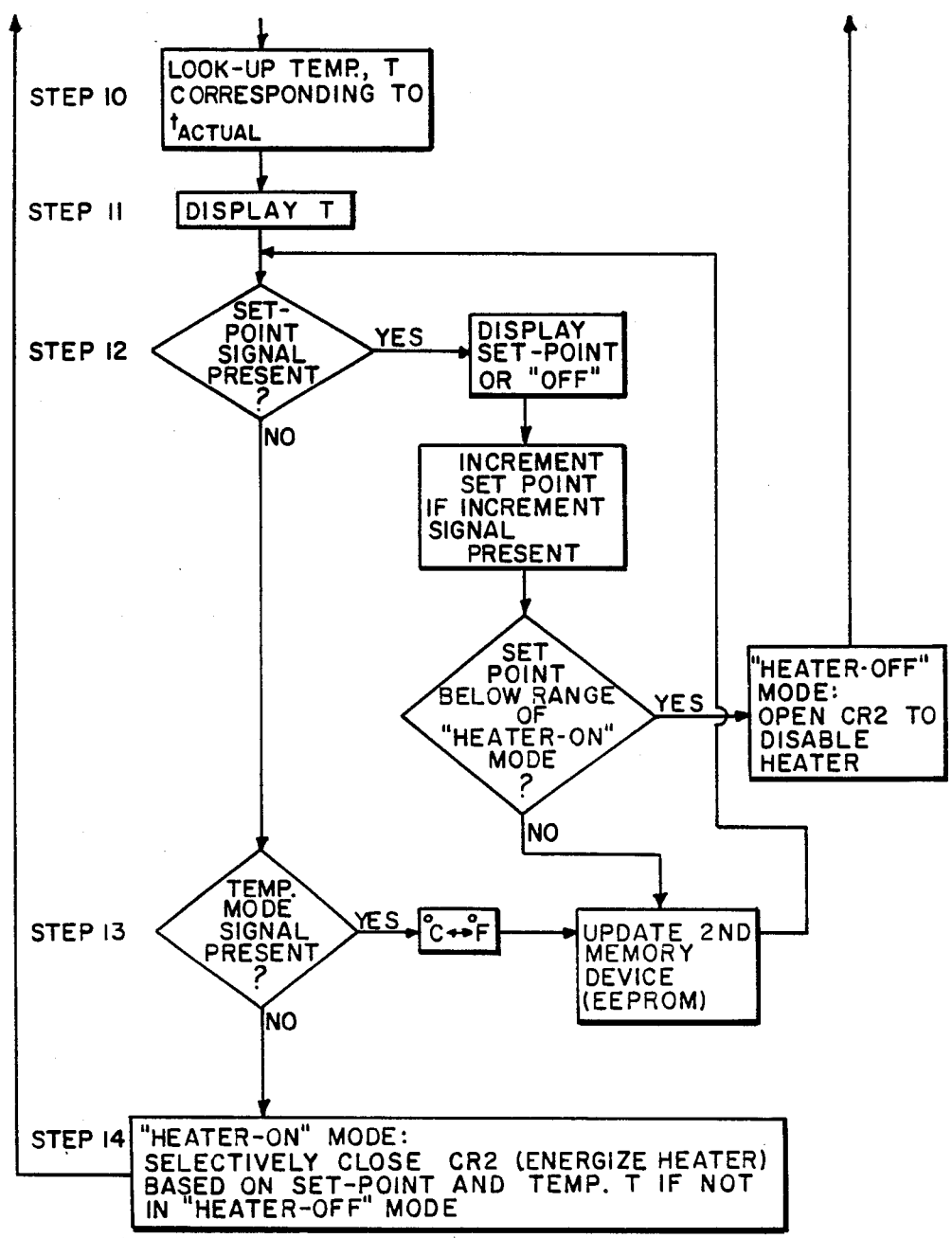
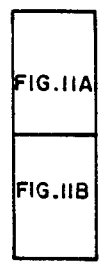
FIG. 11B
FIG. 11

LIQUID-CIRCULATING THERMAL THERAPY SYSTEM

FIELD OF THE INVENTION

The present invention relates to thermal therapy systems of the type wherein a hot or cold liquid is circulated through a pad placed in thermal contact with a patient.

BACKGROUND OF THE DISCLOSURE

It is common practice to treat injured areas of the human body with a hot or cold compress as an aid in the healing process. Localized thermal transfer involves the application of cold or heat, either dry or moist, to a specific area of the body to provide one or more of the following therapeutic affects:

| Cold Therapy | Heat Therapy |
| --- | --- |
| Decrease Blood Flow | Increase Blood Flow |
| Decrease Edema | Decrease Swelling |
| Decrease Hemorrhage | Prevent Tissue Encrustation |
| Decrease Inflammation | Promote Wound Drainage |
| Decrease Muscle Spasm | Decrease Muscle Spasm |
| Decrease Pain | Decrease Pain |
| Provide Patient Comfort | Provide Patient Comfort |

The therapeutic indications for localized cold or heat therapy are extensive. Many conditions call for application of either modality depending on how soon the treatment is initiated. For example, in orthopedic cases, if treatment begins within the first 48 hours after the injury occurs, cold therapy is usually instituted. Thereafter, heat therapy is the preferred mode of treatment. Thermal therapy comprising applications of cold, heat or some combination of the two is useful for a variety of conditions including acute injuries, arthritis, bruises, cellulitis, chronic pain, low back pain, muscle spasm, post-op, sprains, strains, wounds, alopecia, abscesses, headaches, nose bleeds, burns, circulatory disorders, infection, IV infiltration, neuritis, phlebitis, and tendonitis.

In the past, heat has been applied using electric heating pads, hot packs, heat lamps, hot water bottles, hot towels or paraffin baths. Cold has been applied using ice bags, cold packs, cold compresses or cold water bottles. All of these have significant drawbacks, the most obvious being that of inadequate temperature control. This is especially true when extended sessions of treatment are required. A more convenient way of applying such a compress known in the prior art is with a flexible pad having internal passages through which is circulated a warm or cold fluid, usually water, by means of a pump. Typically, the pump assembly includes a reservoir for the liquid, a heater to warm the liquid when desired and means for selecting a desired temperature and maintaining the liquid at that temperature. When a cold compress is desired, the heater is switched off and the reservoir filled with ice water.

The fluid-circulating thermal therapy systems of the prior art also suffer from a number of problems. First, the thermal pads of the prior art fail to provide simultaneously the properties of a highly absorbant, non-slip, non-linting surface with good moisture retention for moist thermal therapy along with good wet strength and a lofty, cushioned feel in a material which is sanitary, relatively inexpensive and readily bonded to the underlying layers of the pad. Non-linting properties are particularly important since migration of fibers into a wound may cause a granuloma to be formed. Secondly, prior art systems fail to provide an indication of the actual temperature of the circulating fluid. Those that provide any temperature indication at all, show only the set-point temperature. They provide no means to determine whether the set-point has been reached or is being properly maintained. Accordingly, to protect the patient there is a need for a system that provide for monitoring the actual fluid temperature as well as the set-point. Third, it is desirable to prevent the patient or other unauthorized persons from altering the temperature set-point prescribed by a physician. According to the prior art this is accomplished by making the set-point adjustment means accessible by way of a key. This requires the nurse or other person in charge to carry the key which is of course subject to being lost or forgotten during a trip to the patient's room. Accordingly, there exists a need for a thermal therapy system which does not require a key but which nonetheless prevents unauthorized persons from altering the temperature set point. Fourth, the systems of the prior art fail to provide a means for directly sensing the water level in the area of the heater and de-energizing the heater when the water in that area drops below a safe level. Instead, these systems rely upon a thermostat to sense the resulting temperature rise in the area of the heater. This is undesirable because under conditions of a rapid temperature rise, such as when an immersion heater runs dry, a thermostat may permit a substantial overshoot in temperature before operating to interrupt power to the heater. Fifth, prior art fluid-circulating thermal therapy systems did not provide a means for de-energizing both the pump and the heater when the unit was tilted beyond a safe angle. Finally, prior art systems must be manually calibrated to insure that the indicated set-point temperature corresponds to the true temperature at which the fluid is being maintained. Calibration can change for a variety of reasons. As the electronic components associated with the temperature measurement and control functions age, their physical characteristics undergo gradual changes which affect the accuracy of temperature measurements. Perhaps more important than gradual aging are the rapid changes in characteristics these electronic components exhibit as the temperature and humidity of the environment in which they operate change. This is extremely significant in a fluid-circulating thermal therapy system since the temperature and humidity in the area where the electronics operate vary over the operating cycle of the unit. For example, when the system is first energized, the temperature and humidity within its housing are very close to the ambient conditions of the room in which the system is located. As the heater warms up, the temperature and humidity in the area of the electronic components rise over the period of an hour or so until they finally stabilize at a steady state.

Even if care has been taken to calibrate the unit after a long warm-up so it is accurate under stabilized conditions, the unit may operate with impaired accuracy for a significant period of time before steady state temperature and humidity are reached. Such inaccuracies cannot be corrected in units constructed according to the prior art since they are not addressed by a routine calibration performed under steady state conditions. Accordingly, there is a need for a fluid-circulating thermal therapy system which calibrates itself at intervals frequent enough to account for changes in calibration occurring as the result of changes in the internal operating environment of the unit during its operating cycle as well as over a period of months or years.

SUMMARY OF THE INVENTION

The present invention includes a number of improvements with regard to fluid-circulating thermal therapy systems.

According to the invention a thermal pad is provided with an external layer of open cell foam material which provides numerous advantages in both moist and dry applications.

The foam layer is secured to the underlying panel of the thermal pad by a wet-proof adhesive, thermal fusion or radio frequency (RF) bonding. The latter two methods are facilitated by impregnating the foam with a bonding agent compatible with the panel material. When wetted for moist thermal therapy, the foam layer remains secured to the panel and exhibits excellent wet strength. The foam material is sanitary, absorbent and offers improved liquid retention to decrease the need for re-wetting during extended sessions of therapy. Wet or dry, the foam layer provides a cushion to help avoid ischemia and to enhance patient comfort.

The invention also includes a float switch to directly sense the amount of liquid available to the heater and to de-energize the heater in the event the quantity is below a predetermined safe level. The float switch may be connected in line with these components to interrupt the flow of electrical current directly on its own or the float switch may act to initiate action on the part of other devices which act in concert to open the circuit. To avoid further reducing the amount of liquid available to the heater under a low liquid condition, the float switch is configured to also de-energize the pump. The invention protects against overheating by utilizing redundant temperature monitoring. Overtemperature protection is provided by a temperature sensor which monitors the temperature of the liquid in the flow path. In the event of a failure of this sensor or associated control circuitry, the temperature sensor is backed up by a limiting thermostat mounted to sense in approximately the same location as the temperature sensor. A second limiting thermostat is located in a second area of the flow path, preferably in the area of the heater to serve as a back-up protector in the event the float switch fails or overheating occurs.

Further according to the invention, a tilt switch reduces the possibility of electrical hazard by operating to de-energize both the heater and the pump when the unit is tilted beyond a predetermined safe angle. To alert personnel of an abnormal condition, the invention includes an audible alarm. The alarm comprises an annunciator which can be triggered under any abnormal condition including one or more of the following: low liquid level, over-temperature and excessive tilting.

When the system operates in the heated mode, a controller heats the liquid in the liquid flow path to a selectable set-point temperature and maintains the liquid substantially continuously at that temperature according to the temperature indication provided by the temperature sensor. The temperature controller periodically recalibrates itself to account for variations caused by aging, changes in humidity, thermal drift and variances in parameters associated with certain electronic components in the temperature sensing portion of the system.

The invention includes display means adapted to display in human perceptible form, the actual temperature of the liquid as sensed by the temperature sensor. In the preferred embodiment, the display means is a dual purpose display adapted to selectively display the actual temperature of the liquid or the set-point temperature. A set-point switch operates to determine whether the actual temperature or the set-point temperature is displayed. Preferably, actuation of the set-point switch also serves to enable a change of the set-point temperature. To operate the unit without heating, the invention contemplates using the means provided to adjust the set-point to disable the heater. This is accomplished by adjusting the set-point beyond the normal operating range of the unit to establish a heater off mode which may be indicated by the display means.

It is also an aspect of the invention to disguise the set-point switch such that its location is identifiable only by authorized persons such as nurses. Such a disguise is readily implemented when the set-point switch is either a membrane switch or a capacitive switch. These types of switches offer flat surfaces which can be made to appear as a decorative label or nonfunctional area of the exterior of the pump assembly.

BRIEF DESCRIPTION OF THE DRAWINGS

FIGS. 11a and 11b show a flow chart illustrating the operation of liquid-circulating thermal therapy system of the invention.

DESCRIPTION OF THE PREFERRED EMBODIMENT

Figure 1:
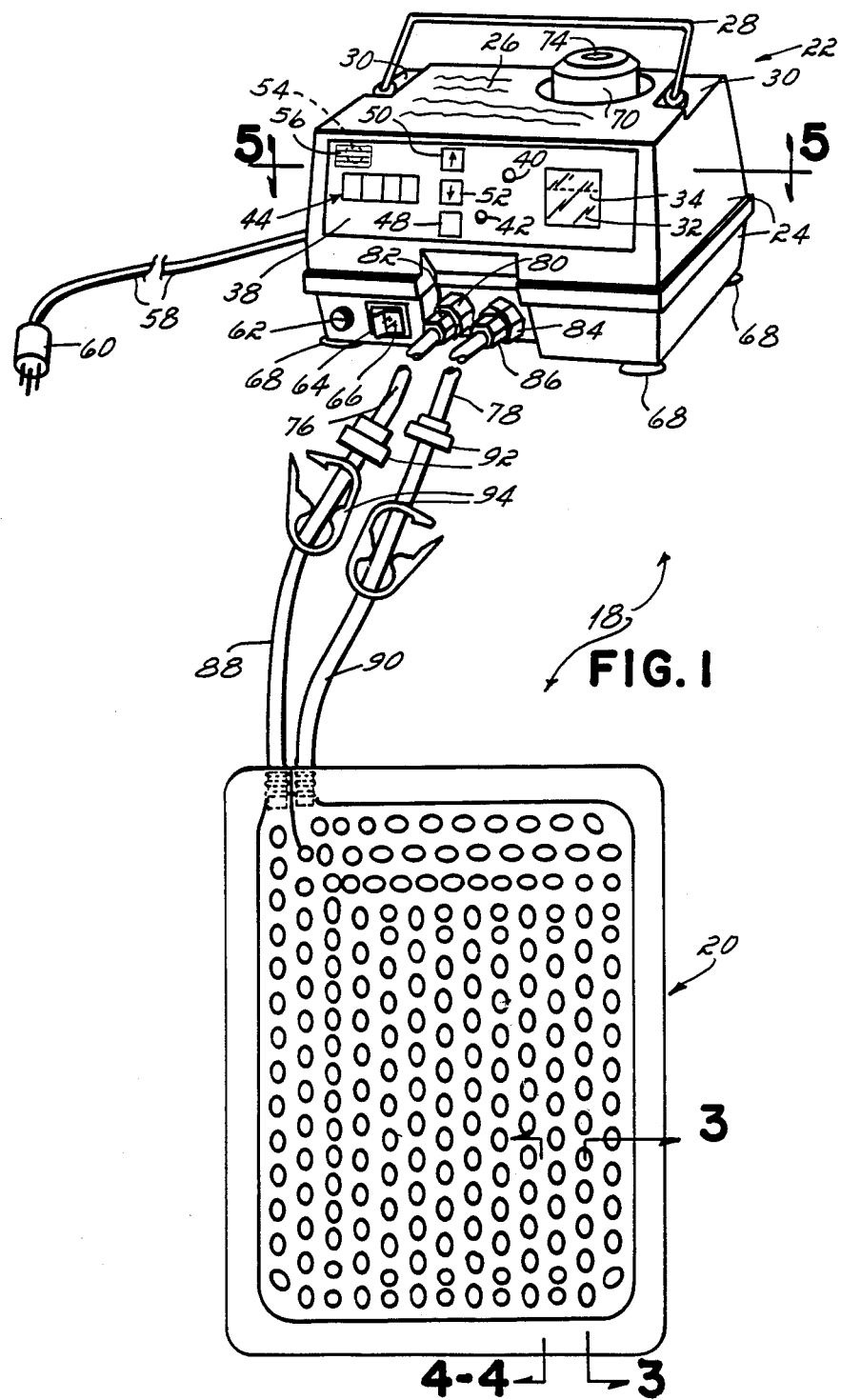
FIG. 1 is a pictorial representation of a liquid circulating thermal therapy system of the invention showing the pump assembly and thermal pad as they are connected in use.

As shown in FIG. 1 a fluid-circulating thermal therapy system 18 comprises generally a thermal pad 20 connected to a pump assembly 22 for circulating a liquid such as water through the thermal pad 22 and optionally heating the liquid to a controlled set-point temperature for heat therapy. The pump assembly is encased by a housing 24 which bears indicia 26 which may include operating instructions, safety precautions or the like. A carrying handle 28 is hingeably secured to housing 24 which includes a recess 30 adapted to receive handle 28 so that handle 28 may be stowed without protruding from the general outline of housing 22 when pump assembly 22 is not being carried. This saves storage space and reduces the chance of pump assembly 22 being knocked over due to bumping or snagging handle 28. Housing 24 has a window 32 for viewing the liquid level 34 present within a translucent reservoir 36 located inside housing 24. Housing 24 also carries a control panel 38 which includes an overtemp light 40, a low-liquid light-emitting diode (LED) 42 and a display 44 for selectively reading liquid temperature or set-point. Low liquid LED 42 is responsive to a float switch 46 mounted within reservoir 36. The state of float switch 46 indicates whether the level of liquid within system 18 is below the desired level 34. Control panel 38 also includes a temperature mode switch 48 to select whether display 46 indicates in degrees Centigrade (°C.) or degrees Fahrenheit (°F.), an increment switch 50 and a decrement switch 52 for raising and lowering, respectively, the set-point temperature. Control panel 38 further includes a set-point switch 54 the actuation of which, causes display 44 to display the set-point temperature. Set-point switch 54 also enables the increment and decrement switches 50,52. Unlike switches 48,50 and 52 which are plainly their function, set-point switch 54 is not so identified except perhaps by an arbitrary symbol 56 for reasons explained below.

Figure 8:
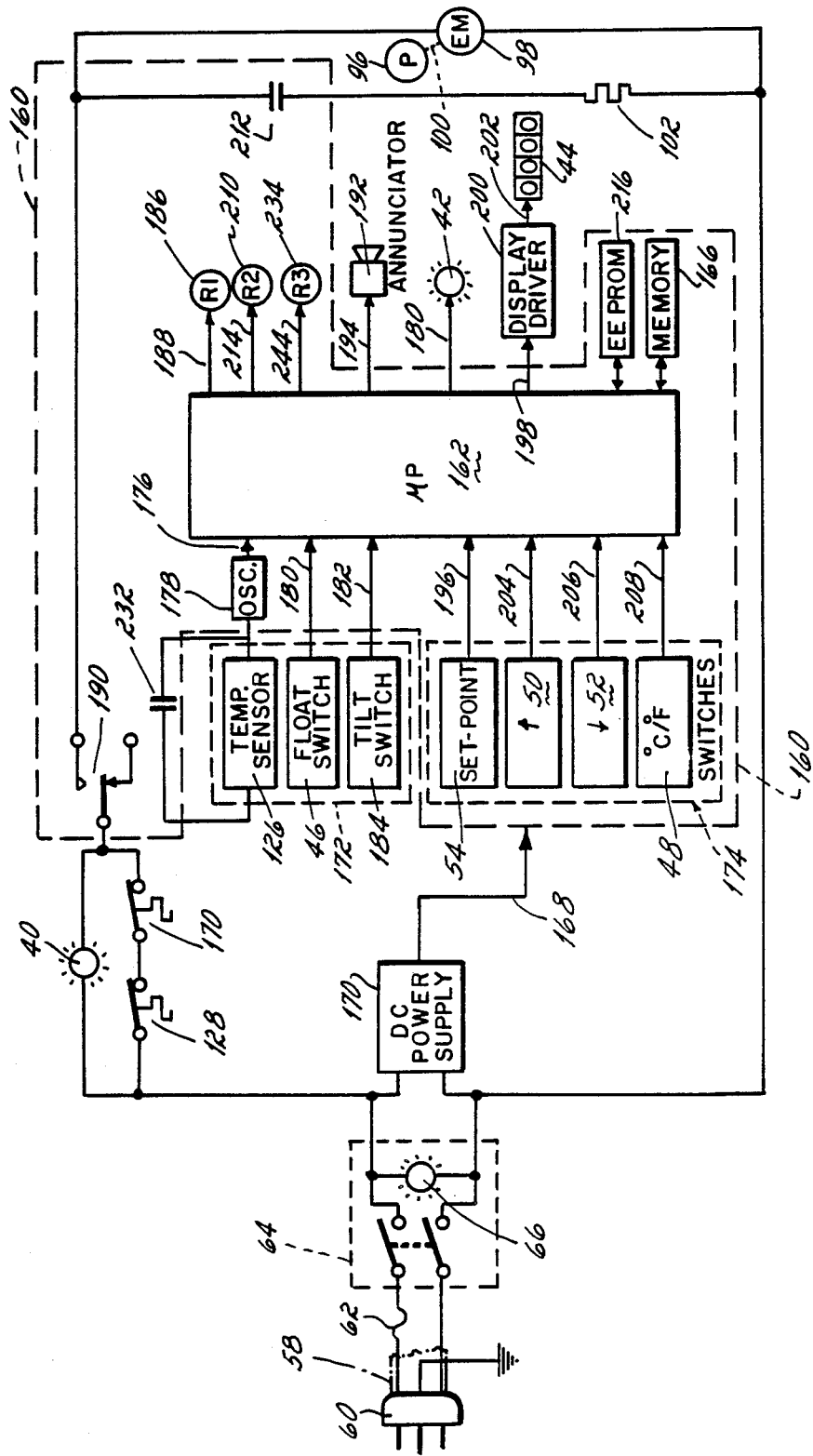
FIG. 8 is an electrical diagram of the thermal therapy system of the invention.

Thermal therapy system 18 also includes a power cord 58 terminated with a grounded, hospital grade plug 60 for connecting the system 18 to an A.C. electrical outlet. Overcurrent protection is provided by fuse means 62 mounted to housing 24 as to be readily accessible from the outside of pump assembly 22. Fuse means 62 is wired in series with power cord 50 as shown in FIG. 8. System 18 is switched "off" and "on" by a power switch 64 wired in series with fuse means 62 and mounted to housing 24 adjacent fuse means 62. Advantageously, power switch 64 includes a light 66 wired across the A.C. line to indicate system 18 is "on" as well as to determine that fuse means 62 has not opened to interrupt the flow of electrical current. Light 66 is connected across the load side of power switch 64 to glow when electrical power is supplied to the unit and power switch 64 is in the "on" position so long as fuse means 62 is not open-circuited.

Pump assembly 22 is supported by a plurality of suction cup feet 68 mounted to the bottom of housing 24. These serve to securely anchor pump assembly 22 to a supporting surface in the event it is bumped. Anchoring also inhibits any tendency the pump assembly 22 may have to move on account of vibration. Suction cup feet 68 also serve to isolate any vibration generated by pump assembly 22 from its supporting surface to provide the quietest possible operation to avoid disturbing the patient's rest.

A removable cap 70 screws onto reservoir 36 over a filler hole 72 atop housing 24 to retain liquid within thermal therapy system 18. Filler cap 70 includes a vent 74 to avoid an excessive buildup of pressure within the system 18. Pump assembly 22 communicates with thermal pad 20 by way of an outlet hose 76 and an inlet hose 78. One end of outlet hose 76 is selectively connected to an outlet port 80 by way of a connector 82 while one end of inlet hose 78 is selectively connected to an inlet port 84 by way of a second connector 86. Thermal pad 20 includes a first inlet tube 88 and a second outlet tube 90 which are connected to the other ends of outlet hose 76 and inlet hose 78 by a pair of connectors 92. Either hose 76,78 may be connected to either tube 88,90 since thermal pad 20 does not require a particular direction of liquid flow. Each tube 88,90 is optionally equipped with a clamp 94 which is open while system 18 is in operation but which may be closed when thermal pad 20 is disconnected from hoses 76 and 78 after use to avoid spilling any liquid remaining inside thermal pad 20.

Figures 2, 3, 4:
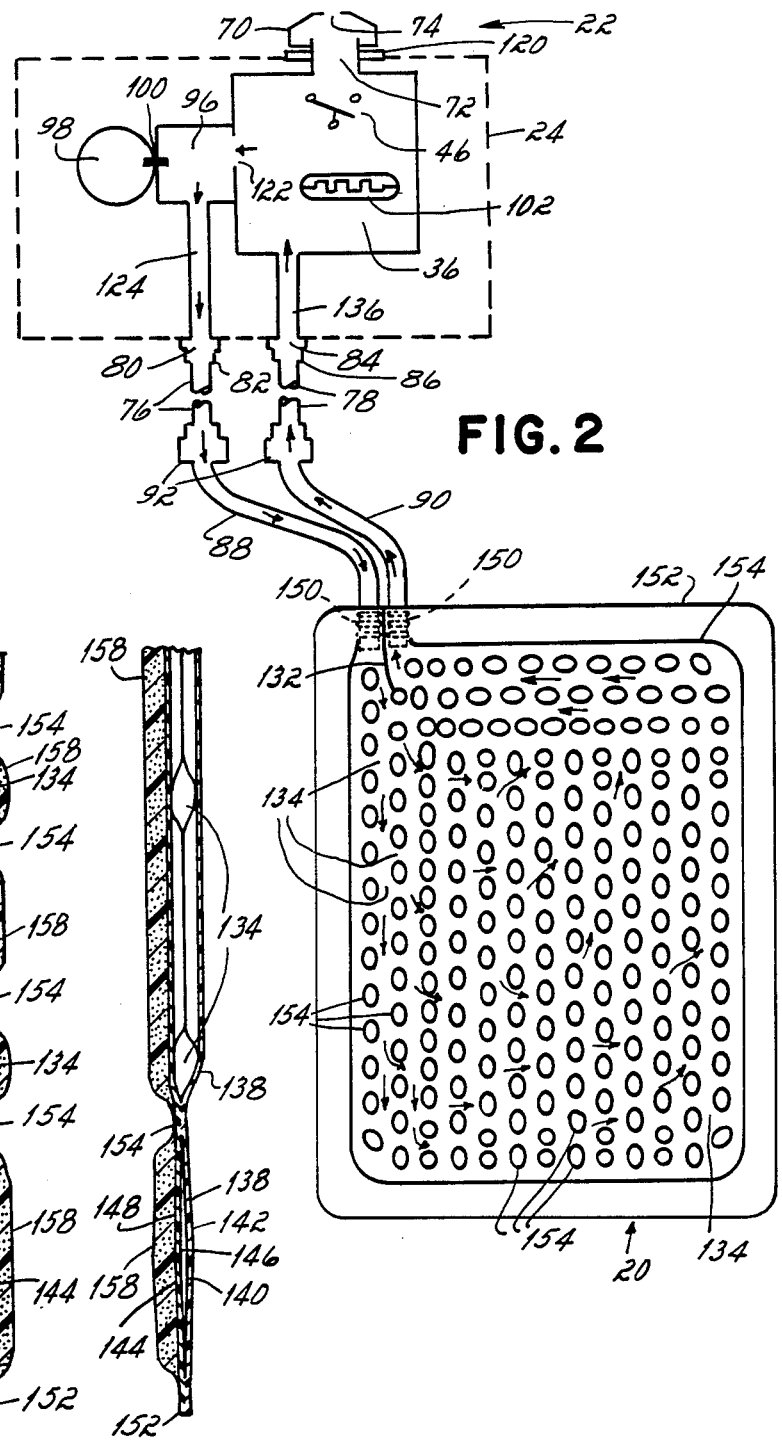
FIG. 2 is a liquid flow diagram for the liquid circulating thermal therapy system of the invention.
FIG. 3 is a partial cross section of a thermal pad of the invention taken along line 3—3 of FIG. 1.
FIG. 4 is a partial cross section of a thermal pad of the invention taken along line 4—4 of FIG. 1.
Figure 5:
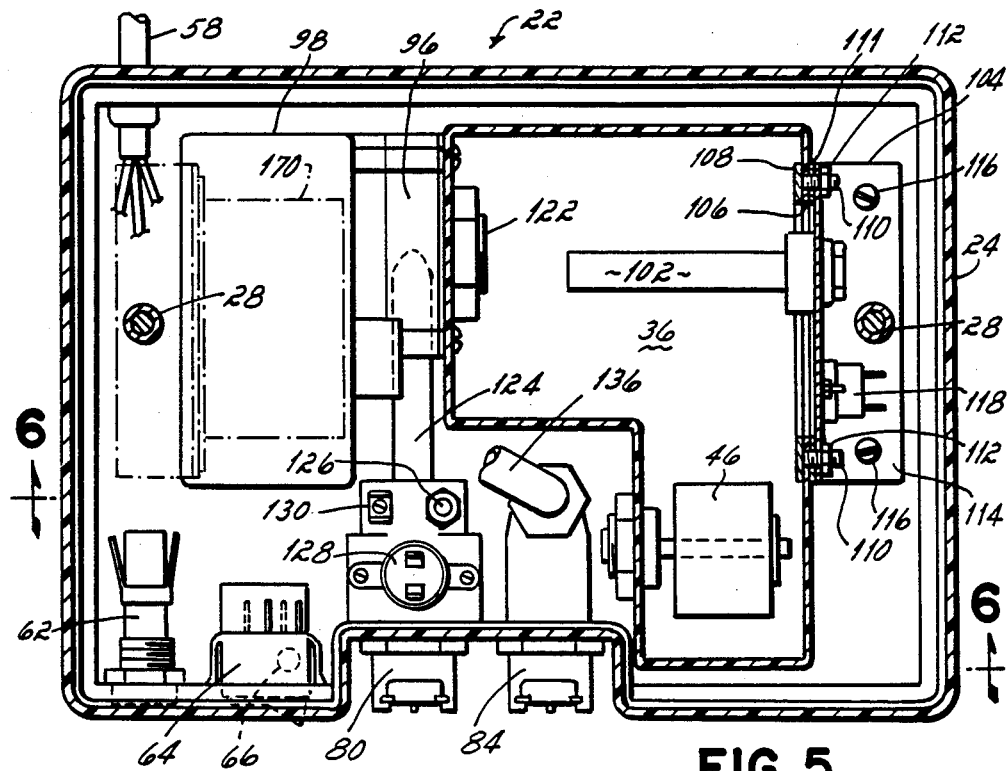
FIG. 5 is a plan section of a pump assembly of the invention taken along line 5—5 of FIG. 1.
Figure 6:
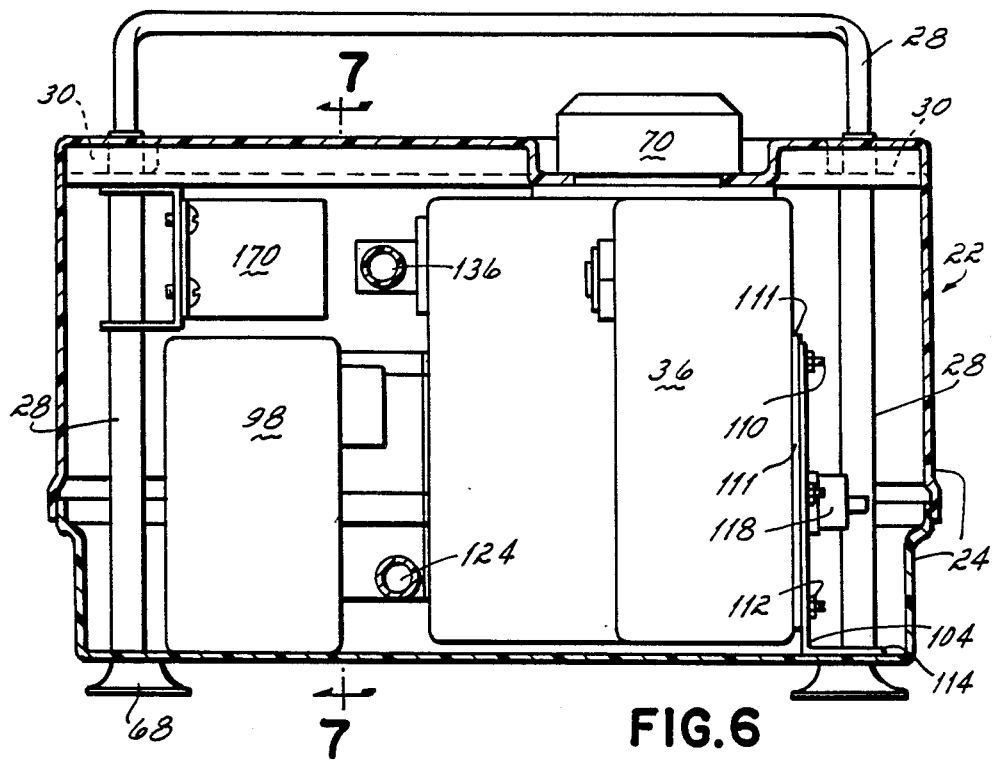
FIG. 6 is a section of a pump assembly of the invention taken along line 6—6 of FIG. 5.

FIG. 2 is a liquid flow diagram which illustrates the flow of liquid within thermal therapy system 18. Within the housing 24 of pump assembly 22 is a pump 96 in communication with reservoir 36. Pump 96 includes an electric motor 98 which provides pump 96 with a source of motive power through shaft 100. Prior to operation, a liquid, preferably water, is added to reservoir 36 in sufficient quantity to raise the liquid level in system 18 to liquid level line 34 visible through window 32. Filler hole 72 is large enough to pass ice cubes which may be added to the liquid in reservoir 36 for cold therapy. System 18 is selectively operable in either of two operating modes; a "heater off" mode for cold therapy and a "heater on" mode for heat therapy. For heat therapy, a heater 102 is selectively energized to heat the liquid to a controlled set-point temperature as will be described further below. Heater 102 is an immersible heater located in the liquid flow path, preferably inside reservoir 36 below the normal liquid level 34. Heater 102 is secured to a metallic mounting plate 104 which is secured over an aperture 106 in the wall of reservoir 36. Mounting plate 104 is secured to reservoir 36 by a support ring 108 located inside the reservoir wall around the outside of aperture 106. Support ring 108 includes threaded studs 110 which pass through the wall of reservoir 36 and through a sealing gasket 111 interposed between the outer wall of reservoir 36 as well as through mounting plate 104. Nuts 112 secure mounting plate 104 to studs 110. An L-shaped projection 114 extending from the lower end of mounting plate 104 includes one or more fasteners 116 which secure reservoir 36 to the bottom of housing 24. Also secured to mounting plate 104 is a second limiting thermostat 118 which senses the temperature inside reservoir 36 by thermal conduction through mounting plate 104.

After reservoir 36 is filled with liquid to the proper liquid level 34, filler hole 72 is covered with cap 70. A gasket 120 is provided beneath filler cap 70 to insure a liquid-tight seal. When power switch 64 is turned on, motor 98 is energized and pump 96 causes the liquid in system 18 to circulate in a closed flow path comprising a complete loop between and including reservoir 36 and thermal pad 20. Liquid flow proceeds as follows: liquid is drawn from reservoir 36, into pump 96 through a pump inlet 122 and expelled from outlet port 80 by way of a manifold tube 124 to which is secured a temperature sensor 126 such as a thermistor and a first limiting thermostat 128 both mounted to sense the temperature of the liquid within manifold tube 124. Manifold tube 124 is of a material such as annodized aluminum which has a high thermal conductivity and exhibits good corrosion resistance in the presence of liquid. For electrical safety, manifold tube 124 is provided with a grounding lug 130 or screw which is connected to the ground lead of power cord 58. From outlet port 80, the liquid passes through connector 82 into outlet hose 76. The liquid then passes through a connector 92 into a first inlet tube 88 and into thermal pad 20. To promote the flow of liquid throughout thermal pad 20, a liquid barrier 132 is interposed between tubes 88,90. Inside thermal pad 20 liquid flows through one or more channels 134 which connect first inlet tube 88 and second outlet tube 90. Liquid is discharged from thermal pad 20 by way of second outlet tube 90, through a second connector 92 into inlet hose 78. The liquid then passes through connector 86, inlet port 84 and through an inlet tube 136 to return to reservoir 36 to complete the flow path.

The Thermal Pad

A thermal pad 20 constructed according to the principles of the invention is illustrated in detail in FIGS. 1, 2, 3 and 4 to which reference is now made. Thermal pad 20 comprises a first panel, 138, having an interior surface 140 and an exterior surface 142 and an opposed second panel 144 having an interior surface 146 and an exterior surface 148. Panels 138 and 144 may consist of any suitable material which is flexible and impervious to liquid including thermoplastic materials such as polyurethane or polyvinyl chloride. Panels 138 and 142 may be any suitable thickness selected to provide good tear resistance and puncture resistance while maintaining sufficient flexibility to permit thermal pad 20 to substantially conform to the various contours of the body. Preferably, panels 138 and 142 are made of polyvinyl chloride sheet which may be any thickness in the range of 0.005 to 0.050 inches and most preferably, about 0.010 inches thick.

Disposed between the interior surfaces 140,146 of each panel 138 and 144 respectively, is an end of first inlet tube 88 and second outlet tube 90, tubes 88 and 90 having been previously described above. Each tube 88,90 is secured between panels 138 and 144 to form a liquid impervious joint 150 between panels 138,148 and each tube 88,90. The interior surfaces 140,146 of each panel 138,146 respectively, are joined together at the outer edges of each panel 138,144 to form a liquid impervious edge seal 152. Further within the periphery of each panel 138,144, interior surfaces 140,146 may be joined along an inner seal 154 which terminates at the end of each tube 88,90 as to be continuous with joint 150. Still further within the periphery of panels 138 and 144 interior surfaces 140 and 146 are joined to form one or more interconnected channels 134 through which tubes 88 and 90 communicate as described above. Preferably, interior surfaces 140,146 are joined at a plurality of selected sealed locations 156 such that the interstices between sealed locations 156 define channels 134. Joint 150, edge seal 152, inner seal 154 and the seals at locations 156 may be by any one or a combination of the use of a liquid-proof adhesive, thermal fusion or radio frequency (R.F.) welding.

According to the invention, thermal pad 20 includes a layer of foam 158 contiguous with the exterior surface of at least one of panels 138 and 144 to absorb and retain a liquid such as water when foam 158 is wetted to prepare pad 20 for moist thermal therapy. In both moist and dry thermal therapy, foam 158 provides a lofty, cushioned feel which provides many advantages, among which is the enhancement of patient comfort. A second advantage is perhaps more important from a therapeutic standpoint.

When an area of the human body rests upon a surface, the irregular shape of that body area may cause its weight to be distributed unevenly resulting in localized pressure points in certain areas. At such pressure points, blood flow can be decreased or obstructed causing localized tissue anemia, a condition known in the art of medicine as ischemia. Ischemia is particularly undesirable in heat therapy since the object of such therapy is to increase blood flow in the area of treatment because blood functions as a transport medium carrying beneficial agents to and adverse agents from the treated area to promote healing. The cushion provided by the layer of foam 158 helps to avoid ischemia by distributing body weight at local pressure points over a larger area of thermal pad 20 than would be the case if the layer of foam 158 were not present.

For dry use, foam layer 158 may comprise any suitable non-fibrous, cushiony material. Fibrous materials are undesirable because they generate lint and because migration of a loose fiber into a wound can cause the formation of a nodule of chronically inflamed tissue known as granuloma. So that thermal pad 20 may be used either wet or dry, foam layer 158 preferably comprises a material adapted to absorb liquid when wetted and to retain a sufficient amount of the liquid to feel wet to the touch. Suitable materials for wet or dry use include open-cell foam materials such as soft natural or synthetic sponge. As used herein, the term "open-cell foam" refers to a material which is spongy and includes a plurality of small, porous cavities.

Most preferably, foam 158 is a polyurethane foam which can be made from any typical polyester or polyether that is used to make polyurethane foam materials. Suitable polyether foams include foams of hydroxyl terminated polyethers having a molecular weight of approximately 3,000–6,500 which are based on polyoxypropylene or polyoxyethylene units or adducts of glycerol, trimethyl propane, or 1,2,6-hexanetriol or other similar trifunctional products. These polyethers can also be comprised of combinations of polyethers, for instance polyethers with amine based polyols such as polyoxypropylene or polyoxypolyethylene diamines, triethanolamine, or similar products. Additionally, "polymer polyols" consisting of graft copolymers of polyethylene diols or triols or combinations thereof having grafts of polyacrylonitrile may be used. Other polyester components may include poly (oxytetramethylene) glycols.

Suitable polyester polyols include hydroxyl terminated polyesters such as polyadipates, especially poly (1,4 butanediol) adipates, poly 1,6 hexane adipates, polyethylene glycol adipates, polypropylene glycol adipates, polytetramethylene glycol adipates, either alone or in combination. Other polyesters consist of blends of adipates and phthalates or adipates and isophthalates which may contain triols such as glycerol, or trimethyl propane.

The isocyanates employed are the typical polyisocyanates normally utilized, namely, 2,4 and 2,6 tolune diisocyanate or mixtures, 1,4 diphenyl methane diisocyanate, aliphatic isocyanates such as methylene bis cyclo hexyl diisocyanate, cyclo hexane diisocyanate or similar diisocyanates, alone or in mixtures. Chain extenders such as 1,4 butane diol, ethylene glycol, dipropylene glycol may be used.

Suitable catalysts for the foaming reaction include tertiary amines such as triethylene diamine, available from Air Products Company under the trade name DABCO, N-ethylmorpholine, as well as certain metal catalysts, particularly the organo tin compounds such as stannous octoate, dibutyl tin dilaurate, and similar tin compounds although other organo metallic compounds may also be used. Combination of the tertiary amines with the organo metallic compounds are used for synergistic action and for improved properties.

The blowing agent is preferably carbon dioxide which is generated by the reaction of the isocyanate with the water present in the foam formulation. Auxiliary blowing agents, such as fluorocarbons or methylene chloride may be used to lower the density and provide softer foams. Preferably, foam 158 has a density of about five pounds per cubic foot. Cell geometry and cell size can be controlled using silicone surfactants consisting of copolymers of poly dimethyl siloxanes and polyoxy alkylene glycols.

Suitable foams as described above may be obtained from suppliers such as General Foam Corp., Goodyear, Reeves Brothers and Perma-Foam.

Foam layer 158 is contiguous with the exterior surface 148 of second panel 144 and is preferably joined securely thereto. This joint may be effected by the use of a suitable liquid-proof adhesive, conductive heat fusion or by radio-frequency (R.F.) welding. Foam layer 158 may be secured at sealed locations 156 by any of the above methods, preferably in the same operation in which joint 150, edge seal 152 and inner seal 154 are formed. To facilitate joining foam layer 158 to panel 144 by conductive heat fusion or RF welding, the invention contemplates impregnating foam layer 158 with a material which readily fuses with the material of panel 144 under heat and pressure. For example, where panel 144 comprises a sheet of polyvinyl chloride, foam layer 158 may be impregnated with vinyl prior to joining foam layer 158 to panel 144.

The Controller

Thermal therapy system 18 is governed by a controller 160, the structure and function of which may be understood with primary reference to FIG. 8. Although controller 160 is described herein in terms of a preferred embodiment that is based upon a central processing unit or microprocessor, it should be understood that the controller 160 of the invention is not limited to an apparatus which includes a microprocessor. It will be recognized by one skilled in the art that the principles of the invention may be implemented in many forms which may be analog, digital or combinations of the two and may be constructed from discrete devices alone or in combination with integrated circuit devices. Such alternatives will readily suggest themselves to one skilled in the art in light of the disclosure provided herein.

Figure 7:
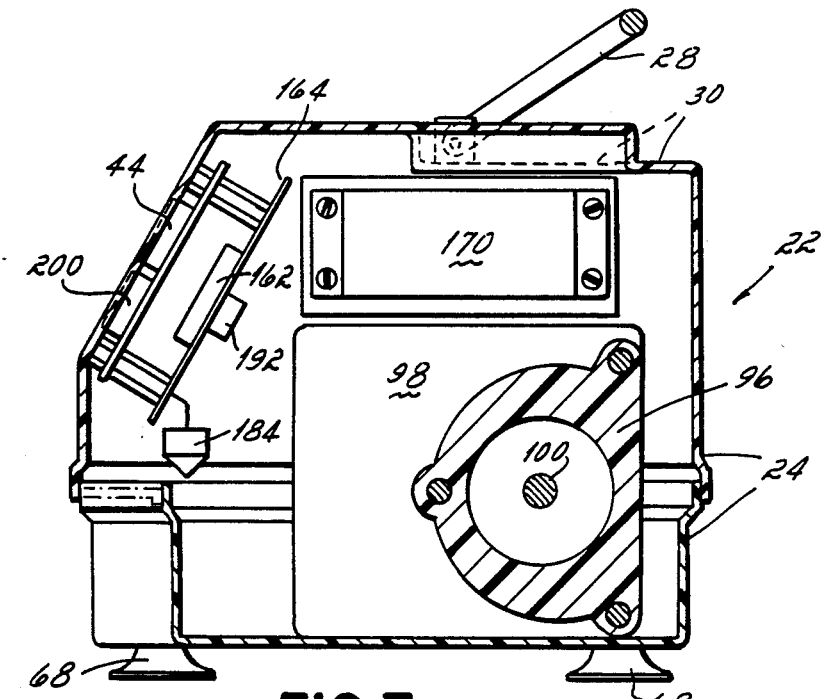
FIG. 7 is a section of a pump assembly of the invention taken along line 7—7 of FIG. 6.

Controller 160 includes central processing unit or microprocessor 162 mounted to a printed circuit (P.C.) board 164 as shown in FIG. 7. Microprocessor 162 operates according to a software program stored in memory device 166. Memory device 166 may comprise a read-only memory (ROM), a programmable read-only memory (PROM), an erasable, programmable read-only memory (EPROM) or other device suitable for storing information for use by a central processor. Controller 160 receives D.C. power 168 from a D.C. power supply 170 which is connected in series with power switch 64.

Microprocessor 162 receives information emanating from a group of three sensors 172 located inside housing 24 as well as from a group of four switches 174 mounted on control panel 38. This information is processed by microprocessor 162 according to the program stored in memory 166, causing microprocessor 162 to generate signals to control pump motor 98 and heater 102 as well as to provide useful audible and visible information about the present status of the system 18.

More particularly, microprocessor 162 receives a temperature signal 176 from an oscillator 178 whose output varies in frequency according to the temperature of the liquid in system 18 as sensed by temperature sensor 126 mounted on manifold tube 124.

Microprocessor 162 also receives a low-liquid signal 180 in accordance with the state of float switch 46 to indicate whether or not the quantity of liquid in reservoir 36 is below a predetermined amount. It is important to insure that sufficient liquid is available to heater 102 to prevent heater 102 or other components from reaching excessive temperatures.

Should float switch 46 fail to operate when the liquid level is too low, second limiting thermostat 118 will operate to de-energize both pump motor 98 and heater 102. Second limiting thermostat 118 is selected to open at about 117 degrees Fahrenheit. In addition to providing a safety device as a back-up to float switch 46, second limiting thermostat 118 also provides redundant over-temperature protection in the event temperature sensor 126 or controller 160 fail. An additional level of over-temperature redundancy is provided by first limiting thermostat 128 mounted to manifold tube 124. Thermostat 128 is selected to open at about 112 degrees Fahrenheit. Should either thermostat 128 or 118 open, the over-temperature light 40 mounted on control panel 38 will glow to alert the operator. A further level of over-temperature protection is also provided by controller 160 as will be discussed below.

Microprocessor 162 also receives a tilt signal 182 in accordance with the state of a tilt switch 184 which changes state when pump assembly 22 is tilted beyond a predetermined safe angle from horizontal which is the normal operating position of pump assembly 22. Tilt switch 184 may be any device which changes state when tilted beyond a predetermined angle. If desired, tilt switch 184 may be wired directly in series with heater 102 and pump 96 so that both components are de-energized when pump assembly 22 is tipped over. More preferably, tilt switch 184 communicates with some other device such as controller 160 as shown in FIG. 8, controller 160 being effective to de-energize pump 96 and heater 102. During operation, relay R1, 186 is energized by microprocessor 162 according to a first relay signal, 188 so that contact CR1 190 is closed to provide power to heater 102 and motor 98. When tilt switch 184 is tripped, controller 160 is programmed to de-energize relay R1, 186 as to open contact CR1 190. Relay CR1 190 remains de-energized until the abnormal condition is cleared.

Alternatively, controller 160 could be configured to maintain heater 102 and pump 96 in a de-energized state after tilt switch 184 has been tripped even if pump assembly 22 is promptly uprighted. This would help to assure that system 18 is examined for damage by a trained operator before being put back into operation after tipping over. Preferably, tilt switch 184 comprises a sealed, mercury switch which may be mounted to P.C. board 164 as shown in FIG. 7.

Also mounted to P.C. board 164 is an annunciator 192 which provides an audible alarm which sounds when one or more of the following occur: float switch 46 changes state to indicate the level of liquid in reservoir 36 is too low, temperature sensor 126 senses a liquid temperature which exceeds a predetermined limit or tilt switch 184 senses that pump assembly 22 has been tilted beyond a predetermined safe angle. In the preferred embodiment shown in FIG. 8 annunciator 192 sounds according to an annunciator signal 194 generated by microprocessor 162. However, it should be understood that within the principles of the present invention, annunciator 192 may be actuated by temperature sensor 126, float switch 46 or tilt switch 184 either directly or in combination with other devices.

In addition to receiving and acting upon signals from the group of sensors 172 as just described, controller 160 is also responsive to external commands from a human operator which are entered from a group of switches 174 located on control panel 38. Switches 174 include set-point switch 54, increment switch 50, decrement switch 52 and temperature mode switch 48.

Set-point switch 54 causes the current set-point temperature to be displayed by display 44. When actuated, set-point switch 54 sends a set-point signal 196 to microprocessor 162. Set-point signal 196 prompts microprocessor 162 display to send a display driver signal 198 to display driver 200, display driver signal 198 being operative to cause display driver 200 to send a display signal 202 to display 44, display signal 202 being operative to cause display 44 to display the current set-point.

Preferably, and further according to the invention, set-point switch 54 and set-point signal 196 also enable increment and decrement switches 50,52. When actuated, switches 50 and 52 cause microprocessor 162 to raise or lower respectively, the set-point temperature in response to a respective increment signal 204 or a decrement signal 206. To "enable" switches 50,52 means to make microprocessor 162 responsive to their actuation. Microprocessor 162 is programmed to ignore actuation of either increment switch 50 or decrement switch 52 unless set-point switch 54 is also actuated. In other words, unless a set-point signal 196 is received by microprocessor 162, actuating the increment and decrement switches 50,52 will not be effective to alter or display the set-point temperature.

It should be noted that the invention does not depend on the use of separate increment and decrement switches 50,52. Some other device such as thumbwheel switch (not shown) could be used to adjust the set-point temperature. As with separate increment and decrement switches 50,52, such a device could be enabled by set-point switch 52 as described above.

Preferably, set-point switch 54 is a momentary contact switch which must be held in the actuated position while either the increment switch 50 or the decrement switch 52 is actuated in order to alter the set-point temperature. When set-point switch 54 is released, increment switch 50 and decrement switch 52 are disabled. Upon releasing set-point switch 50, display 44 ceases to display the set-point temperature and resumes displaying the temperature of the liquid as sensed by temperature sensor 126.

Further, according to the invention, set-point switch 54 is disguised or otherwise concealed while being readily accessible from outside pump assembly 22 so that it may be actuated by persons knowing its location without the use of any special key or tool and without the need to enter housing 24. At the same time, set-point switch 54 is inconspicuous to unauthorized persons who are not trained to identify its location. Consequently, unauthorized persons are less likely to alter the set-point temperature prescribed by the patient's physician.

In addition to the functions previously mentioned, set-point switch 54 may be used to identify the generation of software present in a particular system 18. This may be accomplished by causing programming microprocessor 162 to generate a software identification code to be shown on display 44 when set-point switch 54 is actuated along with some other switch. For example, a software code could be displayed when set-point switch 54 is actuated while power switch 64 is turned "on".

Yet further according to the invention, the location of set-point switch 54 is optionally identified by an arbitrary symbol 56 so that a person trained in the operation of thermal therapy system 18 may readily locate set-point switch 54 without fumbling. Symbol 56 may be any marking which does not reveal or suggest that it relates to the control of thermal therapy system 18. An ideal choice for symbol 56 is the manufacturer's logo.

In selecting a switch for use as set-point switch 54, the invention contemplates using a switch having a profile which is substantially flat so that it may be readily concealed or disguised. Two such types of switches are membrane switches and capacitive switches. In addition to being flat, these switches offer a number of other advantages in a liquid-circulating thermal therapy system. They are readily produced in assemblies having a plurality of switches so that set-point switch 54, decrement switch 52, increment switch 50 and temperature mode switch 48 can be fabricated simultaneously. Further, such a switch can be sealed to be impervious to dust, liquids, vapors or other contaminants to provide protection against humidity or moisture which may be present in the operating environment of the system 18.

To change the display mode from degrees Fahrenheit to degrees Centigrade or vice versa, a temperature mode switch 48 sends a temperature mode signal 208 to microprocessor 162 when temperature mode switch 48 is actuated. The presence of temperature mode signal 208 causes microprocessor 162 to change the present display mode by way of display driver signal 198 and corresponding display signal 202. Whichever temperature mode, °C. or °F. is selected, both liquid temperature and set-point are displayed in that mode until the mode is changed by again actuating temperature mode switch 48.

When thermal therapy system 18 is operating in the "heater on" mode, controller 160 operates to control the temperature of the liquid at the selected set-point temperature. Closed-loop control is effected by controller 160 according to feedback provided by temperature signal 176 which indicates the temperature of the liquid within the manifold tube. In response to temperature signal 176, microprocessor 162 selectively energizes heater 102 by energizing relay R2,210 to close contacts CR2,212 to warm the liquid within system 18 to the set-point temperature. Relay R2,210 is actuated according to a second relay signal 214. Once the set point is reached, the set-point temperature is maintained using relay R2,210 to selectively energize and de-energize heater 102.

The mode of temperature control employed is determined by the software program stored within memory 166. Simple "ON-OFF" control can be used whereby heater 102 is energized when temperature signal 176 indicates the liquid temperature is below the set-point and de-energized when temperature signal 176 indicates the liquid temperature is above set-point. However, because simple "On-Off" control may result in a less accurate control due to temperature overshoot and undershoot, it may be desireable to employ a more sophisticated mode of control. Controller 160 may be programmed to execute proportional control, derivative control, integral control or any combination of them, such methods of control being well known in the art of temperature control.

As previously noted, controller 160 also provides over-temperature protection. An upper limit temperature is included within the program stored in memory 166. According to the program, microprocessor 162 compares the temperature indicated by temperature signal 176 with this upper limit temperature. If the liquid temperature exceeds the limit temperature, microprocessor 162 de-energizes heater 102 and generates an annunciator signal 174 which causes annunciator 192 to sound. As a safety precaution, microprocessor 162 also opens contact CR1,190.

When the thermal therapy system 18 is energized for the first time, the pre-programmed set-point temperature at which controller 160 begins operation is a default value determined by the program stored in memory 166. According to the invention, each set-point subsequently established is stored in a second memory device 216 adapted to retain the set-point information after system 18 has been disconnected from its external power source as when plug 60 is disconnected, fuse means 62 trips or power switch 64 is opened. A device well-suited for use as second memory device 216 is an electrically eraseable, programmable, read-only memory which may also be called an EE PROM or $E^2$-PROM. Such a device is preferred since it retains information for extended periods without any external power source. Upon subsequently turning system 18 on, the set-point value stored in memory device 216 is retrieved by microprocessor 162 and established as the current set-point. This feature avoids the nuisance of having to re-set the set-point each time power may be interrupted. It also reduces the possibility of conducting therapy at any set-point other than one keyed in by a trained operator according to a physician's order. Second memory device 216 is likewise adapted to retain the current temperature mode as selected by the last prior actuation of the temperature mode switch 48 and to make such information available for retrieval by microprocessor 162 when the system 18 is powered up. This avoids any confusion which might otherwise result if display 44 changed from Centigrade to Fahrenheit or vice versa after a power interruption.

Decrement switch 50 is also used to select whether thermal therapy system 18 operates in a "heater on" mode for heat therapy or a "heater off" mode useful for cold therapy. In the "heater on" mode, controller 160 operates to heat the liquid in the system 18 to the set-point temperature selected as described above. When in the "heater on" mode and set-point switch 54 is actuated, display 44 shows the set-point temperature. Otherwise, the actual temperature of the liquid at manifold tube 124 as sensed by temperature sensor 126 is displayed. In the "heater off" mode, controller 160 keeps heater 102 off by causing microprocessor 162 to de-energize normally open relay R2, 210 so that corresponding relay contacts CR2,212 remain open. At the same time, microprocessor 162 maintains relay R1,186 in an energized state so that its normally open contact CR1,190 closes to energize pump motor 98 to circulate unheated liquid. In the "heater off" mode, system 18 displays liquid temperature but does not control it.

Controller 160 is programmed to commence operation according to the set-point and operating mode data stored in second memory device 216 or, in the case of initial operation, according to the default options stored in memory 166. Once the system 18 is started, the operating mode and set-point remain unchanged unless altered by the operator. When power switch 64 is turned "on", display 44 flashes several times to indicate all display segments are functioning. The system 18 then sounds annunciator 192 to demonstrate its operability. Next, the system 18 flashes the pre-programmed set-point temperature several times and commences operation displaying liquid temperature. If the "heater-off" mode has been selected in prior operation, display 44 flashes the word "OFF" instead of the set-point and operation commences with heater 102 disabled. The set-point temperature or operating mode can be changed by actuating the increment or decrement switches 50,52 while the set-point switch 54 is actuated. In response to the presence of set-point signal 196 and decrement signal 206, microprocessor 162 begins to decrement the set point at intervals of about a second. The decreasing set point is simultaneously displayed by display 44. The typical operating temperature range useful for heat therapy has a lower limit of about 78° Fahrenheit and an upper limit of about 107° Fahrenheit. In the "heater on" mode, the set-point may be adjusted within this range. The "heater off" mode is established by controller 160 when the set-point is decremented below the lower limit of the operating range of the "heater on" mode. When the "heater off" mode is reached, microprocessor 162 causes display 44 to provide an indication such as by displaying the word "OFF".

The invention further comprises an apparatus and method for accurately measuring the electrical resistance of a resistive component or a parameter with respect to which resistance varies as a mathematical function. For example, in a liquid-circulating thermal therapy system such as system 18, the invention is applicable to measure the temperature of the liquid being circulated according to the electrical resistance of a thermistor, the electrical resistance of which varies as a function of temperature. Except for precision resistors, the invention avoids the use of high cost, precision grade electrical components and provides for component interchangeability while maintaining accuracy and avoiding the need for external adjustment by providing self-calibration. Although this aspect of the invention is described as it is applied to a thermal therapy system it must be noted that the invention is broadly applicable in any application wherein it is desired to measure either an electrical resistance or some parameter which varies as a function of resistance.

Figure 9:
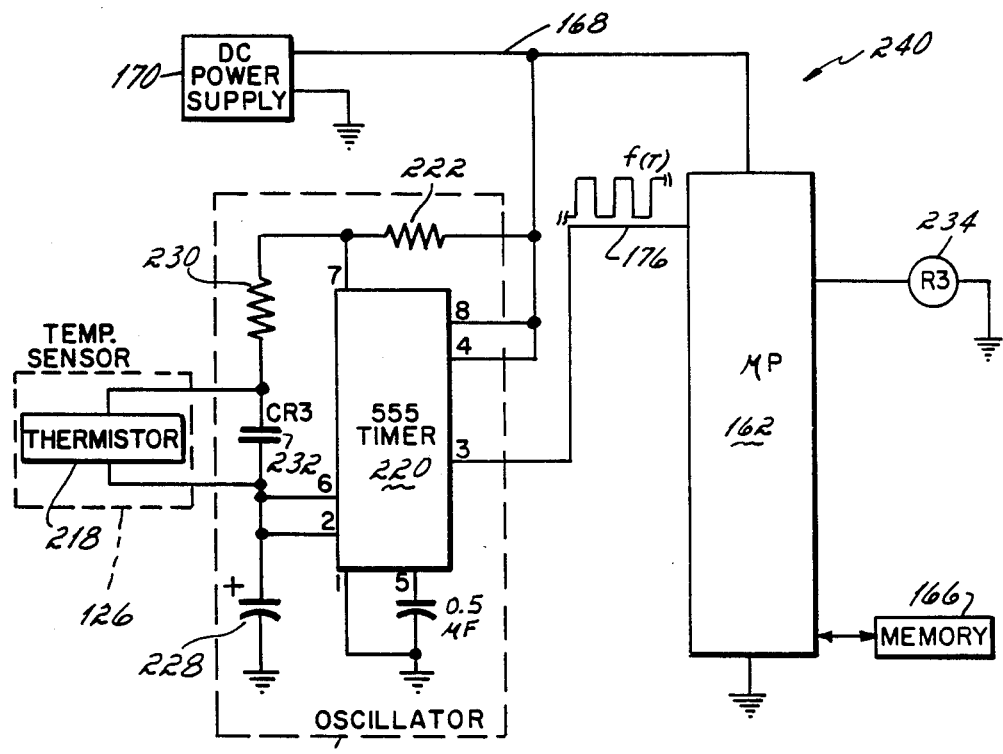
FIG. 9 is an electrical diagram of the self-calibrating apparatus of the invention.

The invention may be further understood with reference to FIGS. 8 & 9. As previously noted, microprocessor 162 determines the temperature of the liquid passing through manifold tube 124 according to the frequency of temperature signal 176 which is generated by a variable frequency oscillator 178. Temperature signal 176 comprises a train of pulses having a frequency f(T) which varies according to the liquid temperature sensed by temperature sensor 126 which is a resistive device such as a thermistor 218. Oscillator 178 may consist of any oscillator suitable for generating a pulse train which varies according to a parameter sensed by a suitable sensor. Such oscillators may be constructed in a variety of ways including using an RC network and a Schmitt trigger or type 555 timer as an astable multivibrator or by connecting a temperature sensitive voltage or current source to a voltage or current controlled oscillator respectively.

Regardless of the circuit used to generate temperature signal 176, microprocessor 162 can determine temperature by measuring the period of time, t required to receive a predetermined number of pulses. The measured time, t is compared to a list of numerical values known to correspond to particular temperatures, such corresponding relationships having been stored in memory 166. The corresponding relationships referred to here are determined by the function according to which resistance varies with the parameter to be determined. In the case of a thermistor, each value of resistance corresponds to a particular temperature. Where the resistive function is non-linear as it is with a thermistor, it is convenient to use a look-up table stored in memory 166 to relate the parameter, temperature in this case, to the measured value of frequency or time, t which is directly related to the resistance of the thermistor. The look-up table may have as many entries as the measurement range and accuracy requirements dictate. Once time, t is determined, it is used by the microprocessor 162 to point to an entry position in the look-up table. The temperature corresponding to that entry position is selected by microprocessor 162 as the liquid temperature, T. Temperature T is displayed by display 44 and used by microprocessor 162 for controlling the liquid temperature when system 18 is in the "heater on" mode.

FIG. 9 shows the apparatus of the invention wherein by way of example and not by way of limitation, oscillator 178 has been constructed from a type 555 timer 220 connected to an RC network to form oscillator 178. The RC network comprises a resistor, 222 connected between pins 7 and 8 of timer 220, pin 8 being connected in common to pin 4 and to D.C. power line 168. Resistor 222 has an ohmic value denoted as X. The RC network further comprises a capacitor 228 having a value of C farads, the anode of capacitor 228 being connected in common to pins 6 and 2 of timer 220, the cathode of capacitor 228 being grounded. Connected between pins 7 and 6 of timer 220, the RC network also includes a second resistor 230 having a value of Y ohms in series with thermistor 218 which comprises temperature sensor 126. Thermistor has a resistance designated r(T) ohms which decreases as temperature, T increases. Connected across thermistor is a relay contact, CR3, 232 which is normally open but which may be selectively closed under program control by microprocessor 162 by energizing associated relay coil R3, 234. Relay contact CR3,232 should have a low contact resistance such that when coil R3,234 is energized CR3 closes to form an almost ideal short circuit across thermistor 218, effectively removing thermistor 218 from the circuit.

The oscillation frequency, f(T) in Hertz of oscillator 178 timer 220 is determined according to equation 1 as follows:

$$f(T) = \frac{K}{(X + 2Z)C} \qquad \text{Eqn. 1.}$$

where: K is a constant and Z is determined by the combined series resistance of resistor 230 and thermistor 218 according to equation 2 as follows:

$$Z = r(T) + Y \qquad \text{Eqn. 2.}$$

By inspection of the above two equations, it can be seen that since r(T) decreases as temperature T increases, the frequency, f(T) of temperature signal 176 will increase with increasing temperature.

If microprocessor 162 is to accurately measure temperature T, based on the frequency, f(T) of temperature signal 176, frequency f(T) should vary almost exclusively as a function of temperature as indicated by the resistance r(T) of thermistor 218. However, equations 1 and 2 reveal that numerous other factors namely X, Y, C and K have an effect on the frequency, f(T) of temperature signal 176. To the extent these other factors are not constant, they introduce error into the temperature measurement. Where those factors vary from one like component to the next, the ability to mass produce accurate systems from stock components of ordinary tolerance is impaired.

Factors X and Y are important but present little practical concern since precision resistors are available at reasonable cost. Such resistors remain quite stable in value over time as well as over a wide range of operating temperatures. The invention requires resistors 222 and 230 to be precision resistors. A 0.1% tolerance is preferred, but less precise resistors e.g. 1% resistors may be used where less accuracy is required.

The next factor to be considered is C, the value of capacitor 228. Unfortunately, precise, stable capacitors are not available at reasonable cost. The same is true of 555 timers or other devices which might be used to construct oscillator 178. K is a constant associated with the oscillator circuitry other than the RC network. For a type 555 timer connected as shown in FIG. 9, the nominal value of K is 1.44. However, there is variation in K among the population of type 555 devices. But for the invention, factors C and K vary sufficiently among components and over time and operating conditions that the technique of measuring temperature based on the frequency, f(T) of temperature signal 176 as described above could not be used to make accurate temperature measurements without calibrating each system 18 at frequent intervals.

Figure 10:
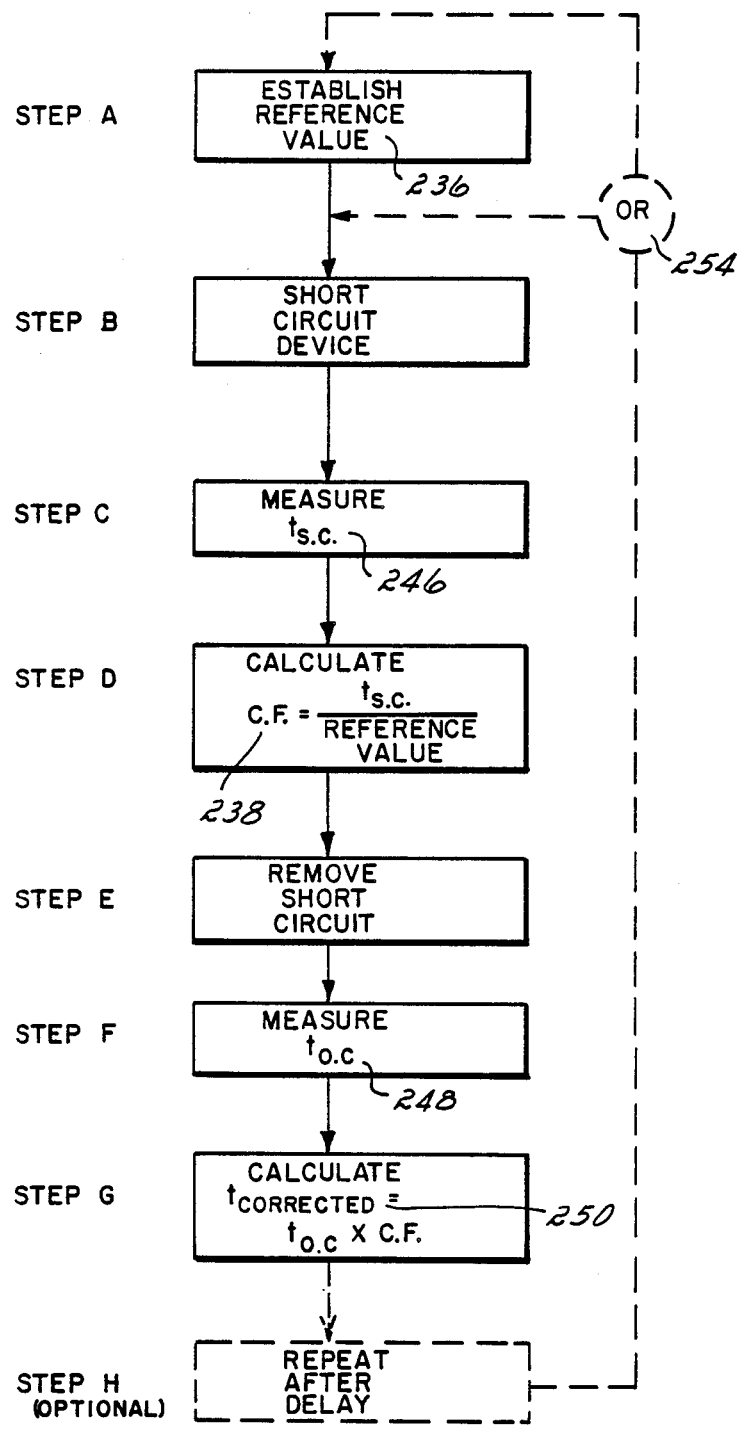
FIG. 10 is a flow chart illustrating the self-calibration method of the invention.

The invention as illustrated in the apparatus of FIG. 9 overcomes the above problems according to the self-calibration method shown in the flowchart in FIG. 10 to which reference is now made.

It should be noted at this point that the method of the invention is not limited to the particular sequence in which the steps are described. Although a preferred sequence is described, it will become apparent to one skilled in the art that a number of alternative sequences of steps may be practiced without departing from the scope of the invention.

Step A comprises establishing a reference value 236. Preferably, reference value 236 is available from a storage device such as memory 166 but it may be entered from other source and at any time so long as value 236 is available for calculating a correction factor, 236 as described below.

Reference value 236 is a value correlated to the frequency of a hypothesized ideal oscillator of the same type as the real oscillator 178 employed in the apparatus of FIG. 9. The difference between the real oscillator 178 and the ideal oscillator is that unlike real oscillator 178, the hypothetical ideal oscillator assumes that thermistor 218 is replaced by a short circuit and has a constant output frequency which remains stable under all conditions and for all time. For example if we assume that the oscillator 178 shown in FIG. 9 is an ideal oscillator in which thermistor 218 is replaced by a short circuit, the ideal output frequency can be calculated from equations 1 and 2 wherein the value of r(T) is assumed to be zero. Reference value 236 is computed by determining the time span between a predetermined number of pulse edges of temperature signal 176 at the ideal frequency. It should be noted that since time and frequency are equivalent in this regard, the invention contemplates making computations either in time, frequency or dimensionless units based upon either quantity. The reference value 236 so established is stored or otherwise made available for subsequent computation.

Step B concerns the real oscillator 176. This step comprises establishing a short circuit across the resistive device, which is represented by thermistor 218 in the apparatus of FIG. 9. This is accomplished under program control by closing relay contact CR3,232 by causing microprocessor 162 to energize corresponding relay coil R3 234 by generating a third relay signal 244. Relay contacts CR3,232 should be selected to provide the least possible contact resistance for best accuracy.

Step C comprises the step of determining the time span required for oscillator 178 to generate a predetermined number of pulse edges when thermistor 218 remains short-circuited. This time span is referred to as $t_{s.c.}$,246. The predetermined number of pulse edges here is the same number referred to in Step A. This number should be selected to be sufficiently large in relation to the expected range of frequencies to provide an accurate indication of frequency.

Step D comprises the step of calculating a correction factor (C.F.),238. Correction factor 238 is defined as a quotient whose dividend is $t_{s.c.}$,246 determined in Step C and whose divisor is the reference value 236 established in Step A.

Step E comprises the step of removing the short circuit across thermistor 218. This may be accomplished under program control by opening relay contact CR3,232 by causing microprocessor 162 to de-energize relay coil R3,234 by removing third relay signal 244. This effectively re-inserts thermistor 218 into the RC network of oscillator 178 so that temperature signal 176 is again responsive to the temperature sensed by thermistor 218.

Step F comprises the step of determining the time required for oscillator 178 to generate the aforementioned predetermined number of pulse edges when relay contact CR3,232 remains open so that thermistor 218 is included in the circuit of oscillator 178. This time span is designated as $t_{o.c.}$,248.

Step G comprises the step of calculating a corrected measurement, $t_{corrected}$, 250 which comprises the product of $t_{o.c.}$,248 and correction factor C.F.,238. The value of $t_{corrected}$, 250 provides an accurate indication of the electrical resistance of thermistor 218 since multiplication by the correction factor 238 eliminates the significant sources of inaccuracy previously discussed. This is so because correction factor, 238 is a dimensionless number the magnitude of which serves as an indication of the degree of error between the operating characteristics of real oscillator 178 and the ideal oscillator previously hypothesized. Thus, when the correction factor 238 equals unity, it means that oscillator 178 is operating as an ideal oscillator. Correction factor 238 accounts for all sources of oscillator error except for factors affecting the resistive elements in the RC network namely, resistor 222, resistor 230 and the thermistor 218.

It is noted that the self-calibrating apparatus and method of the invention also compensates for measurement errors which would otherwise occur if the time base associated with microprocessor 162 drifts for any reason. The time base is the "master clock" of the microprocessor. If the time base began to run faster or slower, the measured value of time required for oscillator 178 to output predetermined number of pulse edges would vary accordingly. If not corrected for, this would cause an incorrect indication of the resistance of thermistor 218 and hence, temperature. The invention avoids this difficulty.

Correction factor 238 accounts for time base variations because reference value 236 is calculated based on the presumptions that an ideal oscillator is completely stable and that its output frequency is determined precisely. In other words, reference value 236 is calculated as though it were being measured by ideal measuring means not subject to time base variation. Thus, when correction factor 238 is applied in Step G of FIG. 10, the effect of time base variations is cancelled out.

Once $t_{corrected}$ 250 has been determined, it may be used to determine temperature according to the look-up table method previously described or by any other suitable method.

Further according to the invention, the self-calibration method described above in Steps A through G may be carried out at periodic intervals. This is shown in FIG. 10 as optional Step H which comprises the step of repeating the prior steps after a delay 252. It should be noted that once reference value 236 has been established, it need not be re-calculated to perform subsequent self-calibrations so long as it is available to perform Step D. This is indicated by the logical "or" operation 254 shown in FIG. 10.

A further aspect of the invention is the manner in which the duration of delay 252 is selected. It is observed that correction factor 238 accounts for certain variations in operating conditions, the magnitude of the correction factor 238 being determined by conditions as they exist at the time the measurement of STEP C is made. Should conditions subsequently change, correction factor 238 will not account for the change unless it is subsequently re-computed. Some conditions such as component aging occur gradually over periods of weeks, months or years depending in part on the duty cycle of the component storage conditions and other factors. On the other hand, conditions such as temperature may change much more quickly. For instance over the operating cycle of the thermal therapy system 18 the temperature and humidity within housing 24 may increase rapidly as the heater 102 brings the liquid up to temperature. Accordingly, the invention contemplates performing self-calibration at intervals frequent enough to account for both gradual and rapid changes in conditions. In a thermal therapy system 18 it is sufficient to self-calibrate at least once every ten (10) minutes and preferably about once every eighty (80) seconds during operation. In other applications, self-calibration may be required more or less often depending on the time constant according to which operating conditions vary.

Figure 11A:
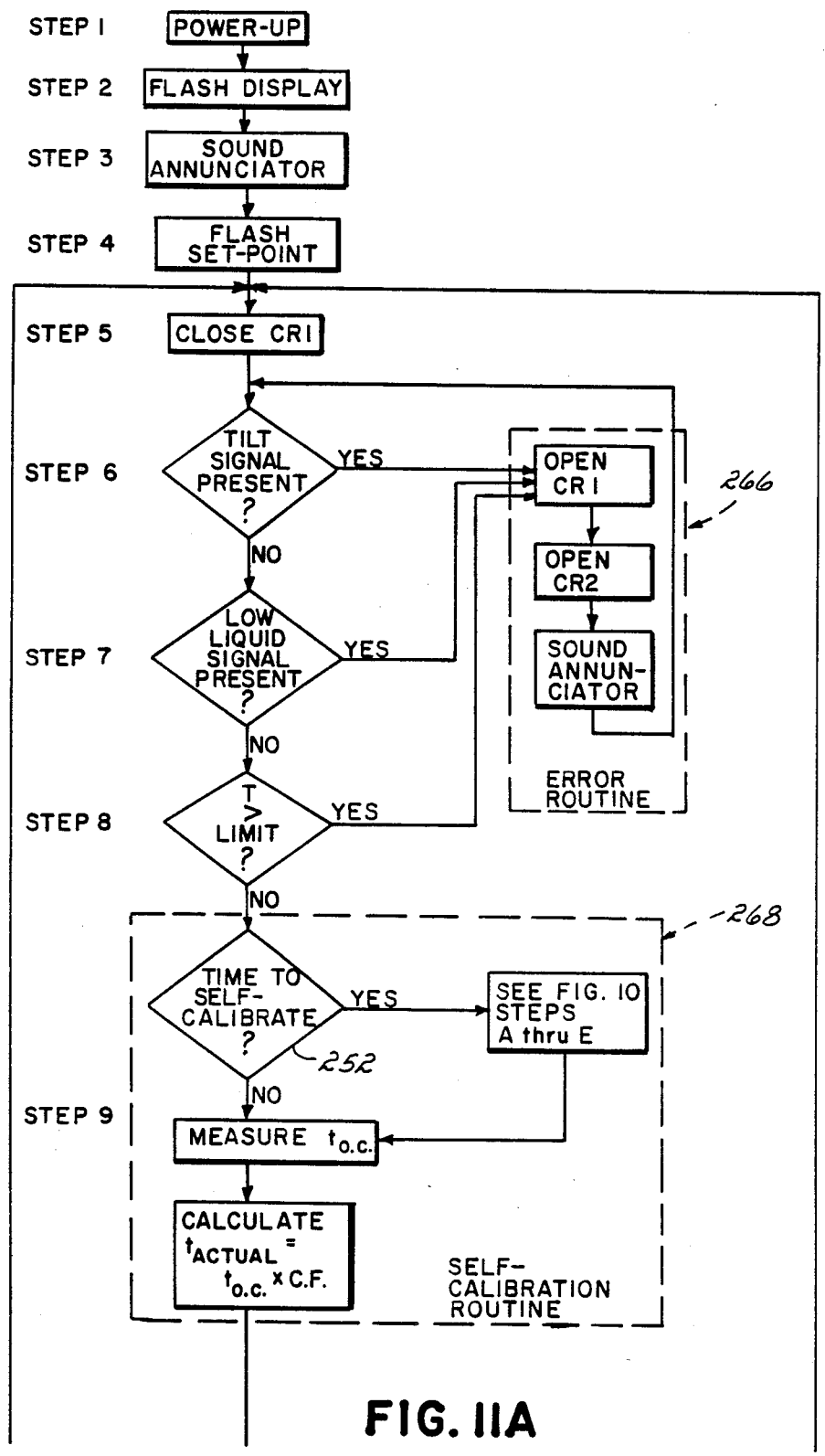

The operation of the liquid-circulating thermal therapy system 18 of the invention can be summarized with reference to the flowchart of FIG. 11.

After the system 18 is connected as shown in FIG. 1 and reservoir 36 has been filled with liquid to the proper liquid level 34, Step 1 of operation is to power-up system 18 by connecting plug 60 to a suitable supply of A.C. power and closing power switch 64. At this point, microprocessor 162 prepares for operation by retrieving instructions and data required from memory 166. During initial operation, the set-point and temperature display mode are determined by default values stored in memory 166. If the unit has been operated previously, set-point and display mode are determined according to data from second memory device 216, the EE PROM.

In Steps 2 and 3, all segments of display 44 are flashed several times and annunciator 192 is sounded to verify the operability of the display 44 and annunciator 192 respectively.

Step 4 consists of flashing the set-point temperature several times to prompt the operator to change the set-point if a different set-point or operating mode is desired.

Step 5 is to close relay contact CR1,190 which starts pump motor 98 and enables heater 102. To close CR1,190 microprocessor 162 generates a first relay signal 188 effective to energize relay coil R1,186.

Steps 6, 7 and 8 comprise a sequence of tests for abnormal conditions, any one of which, if detected, is effective to initiate an error routine, 256 whereby both CR1,190 and CR2,212 are opened to de-energize both heater 102 and pump 96 as well as to sound annunciator 192 to alert the operator. As previously noted, microprocessor 162 can be programmed either to resume operation as soon as the error condition ceases, as shown in FIG. 11 or to latch CR1,190 open until power switch 64 is opened and re-closed. In Step 6, microprocessor 162 checks for the presence of a tilt signal 182 which appears in response to the state of tilt switch 184 when the pump assembly 22 is tilted beyond a predetermined angle from its normal horizontal operating position. In Step 7, microprocessor 162 checks for the presence of a low-liquid signal 180 which appears in response to the state of float switch 46 when the level of liquid in the flow path of system 18 is below a predetermined amount.

In Step 8, microprocessor 162 compares the most recently measured liquid temperature, T with an upper limit temperature included in the software. If the limit is exceeded, the error routine described above is entered. If desired, microprocessor 162 could perform an additional test (not shown) whereby thermistor 218 is checked for open circuiting by checking its resistance against a limit. Should an open circuit be detected, error routine 266 would be entered and an appropriate indication provided by display 44. Otherwise, the system 18 proceeds with normal operation by commencing to the next Step.

Step 9 comprises a self-calibration routine 258 which the system 18 performs at intervals separated by a delay 252 chosen as previously described. The self-calibration routine 258 has been described previously with reference to FIG. 10.

Step 10 comprises determining the liquid temperature value, T which corresponds to the calculated value of $f_{corrected}$ determined in Step 9. This may be done using a stored look-up table as previously described. Alternatively, the liquid temperature, T could be calculated from $f_{corrected}$ or some other value based on the frequency, f(T) of temperature signal 176.

Step 11 comprises the step of displaying the liquid temperature, T, determined in Step 10. The temperature is displayed either in degrees Fahrenheit (°F.) or degrees Centigrade (°C.) according to the temperature mode last selected by way of temperature mode switch 48 or in the case of initial operation, according to the default option stored in memory 166.

In Step 12, microprocessor 162 determines whether set-point switch 54 has been actuated by determining whether a set-point signal 196 is present. If not, the program proceeds to Step 13. If set-point signal 196 is present, the set-point is displayed by display 44. If an increment signal 204 or a decrement signal 206 appears while set-point signal 196 is present, the set-point is incremented or decremented while being displayed. If the set-point is decremented below the operating range of the "heater on" mode, the "heater off" mode is entered. In that case, display 44 indicates the word "OFF" instead of the set-point. In the"heater-off" mode, relay contact CR2,212 is held open to disable heater 102. The system 18 continues operation in the "heater-off" mode until the set-point is again raised to select "heater on" mode. Each change in set-point, including changes which alter the operating mode are stored by the second memory device, 216 so that when the system 18 is switched "off" and subsequently turned "on" again, it will begin operation at the prior set-point or in the "heater off" mode as appropriate.

Step 13 comprises the step of determining whether the temperature mode switch 48 has been actuated by testing for the presence of a temperature mode signal 208. If signal 208 is present, the display mode is changed from the presently established mode, either °F. or °C., to the opposite display mode. Each time the display mode is changed, second memory device 216 is updated. Second memory device 216 stores the most recently established temperature display mode and makes it available for subsequent operation in the same manner as the set-point and operating mode data.

Step 14 comprises the step of selectively closing relay contact CR2,212 to energize heater 102 selectively in dependence upon the latest liquid temperature reading and set-point in order to control the liquid at the set-point temperature. If "heater off" operation has been selected, however, CR2,212 remains open. Regardless of whether "heater-on" or "heater-off" operation is selected, the sequence repeats beginning at Step 5 as shown.

What is claimed is:
1. A liquid circulating localized thermal therapy system including
   a pad having an inlet tube and an outlet tube which communicate by way of a channel within the pad through which liquid is circulated and
   a pump assembly for circulating and heating the liquid, said pump assembly comprising:
   a reservoir for the liquid, said reservoir having an inlet and an outlet;
   a pump for circulating the liquid when said pump is energized from said outlet of said reservoir to said inlet tube of said pad, through said channel and through said outlet tube of said pad to said inlet of said reservoir to define a flow path through which the liquid circulates, said flow path including said reservoir and said channel;
   a heater in thermal contact with said liquid for heating said liquid when said heater is energized;
   a temperature sensor in thermal contact with the liquid for sensing the temperature of said liquid;
   a float switch for sensing the quantity of liquid in said flow path which changes state when the quantity of liquid at a particular location within said flow path is below a predetermined amount; and
   a controller coupled to said temperature sensor and to said float switch including (a) means for energizing said pump and said heater and for de-energizing at least one of said pump and said heater in response to said change of state of said float switch, (b) a set point switch operable to enable selecting or chang- ing a set point temperature of the liquid, (c) set point changing means operable to selectively change said set point temperature when said change has been enabled by said set-point switch and (d) means for energizing said heater selectively in dependence upon the temperature sensed by said temperature sensor in order to effect closed-loop control of the temperature of the liquid about said set-point temperature.

2. A liquid-circulating thermal therapy system as claimed in claim 1 wherein said set-point changing means includes
an increment switch for increasing said set-point temperature and
a decrement switch for decreasing said set-point temperature.

3. A liquid-circulating thermal energy therapy system as claimed in claim 1 further comprising:
temperature display means responsive to said temperature sensor to display in human-perceptible form, the actual temperature of the liquid within said flow path.

4. A liquid circulating thermal therapy system as claimed in claim 3 further comprising:
a temperature mode switch responsive to cause said display means to selectively indicate in either degrees Fahrenheit or degrees Centigrade.

5. A liquid-circulating thermal therapy system as claimed in claim 1 further comprising:
dual display means responsive to said temperature sensor and said controller to selectively display in human-perceptible form one of the actual temperature of the liquid within said flow path or said selected set-point temperature.

6. A liquid-circulating thermal therapy system as claimed in claim 5 further comprising:
a temperature mode switch responsive to cause said display means to selectably indicate in either degrees Fahrenheit or degrees Centigrade.

7. A liquid-circulating thermal therapy system as claimed in claim 5 wherein said set-point switch also operates to select whether the actual temperature of the liquid in said flow path or said selected set-point temperature is displayed by said dual display means.

8. A liquid-circulating thermal therapy system as claimed in claim 1 wherein said set-point switch is disguised to prevent unauthorized persons from changing said set-point temperature.

9. A liquid-circulating thermal therapy system as claimed in claim 1 wherein said set-point switch is a membrane switch.

10. A liquid-circulating thermal therapy system as claimed in claim 1 wherein said set-point switch is a capacitive switch.

11. A liquid-circulating thermal therapy system as claimed in claim 1 further comprising:
a tilt switch for sensing the angular orientation of said pump assembly, said controller being responsive to said tilt switch to de-energize said heater and said pump when said pump assembly is tilted beyond a predetermined angle from horizontal.

12. A liquid-circulating thermal therapy system as claimed in claim 11 further comprising:
an audible alarm responsive to said controller to provide an audible indication upon the occurrence of a predetermined condition wherein said predetermined condition includes at least one of; (a) the liquid in said flow path being in excess of said predetermined temperature limit, (b) the quantity of liquid within said flow path being below said predetermined amount, and (c) said pump assembly being tilted beyond said predetermined angle from horizontal.

13. A liquid-circulating thermal therapy system as claimed in claim 1 further comprising:
an audible alarm responsive to said controller to provide an audible indication upon the occurrence of a predetermined condition wherein said predetermined condition includes at least one of; (a) the liquid in said flow path being in excess of a predetermined temperature and (b) the quantity of liquid in said flow path being below a predetermined amount.

14. A liquid-circulating thermal therapy system including
a pad having an inlet tube and an outlet tube which communicate by way of a channel within the pad through which liquid is circulated and
a pump assembly for circulating and heating the liquid, said pump assembly comprising:
a reservoir for the liquid, said reservoir having an inlet and an outlet;
a pump for circulating the liquid when said pump is energized from said outlet of said reservoir to said inlet tube of said pad, through said channel and through said outlet tube of said pad to said inlet of said reservoir to define a flow path through which the liquid circulates, said flow path including said reservoir and said channel;
a heater in thermal contact with said liquid for heating said liquid when said heater is energized;
a temperature sensor in thermal contact with the liquid for sensing the temperature of said liquid; and
a controller switch coupled to said temperature sensor for energizing said heater selectively in dependence upon the temperature sensed by said temperature sensor in order to effect closed-loop control of the temperature of the liquid about a set-point temperature including (a) a set-point switch operable to enable selecting or changing a set-point temperature of the liquid, and (b) set-point changing means operable to selectively change said set point temperature when said change has been enabled by said set-point switch.

15. A liquid-circulating thermal therapy system as claimed in claim 14 wherein said controller includes a memory means for storing said temperature set-point when said thermal therapy system is de-energized and beginning operation at said stored temperature set-point when said thermal therapy system is next energized.

16. A liquid-circulating thermal therapy system as claimed in claim 15 wherein said memory means comprises:
an elecrically erasable programmable read-only memory device.

17. A liquid-circulating thermal therapy system as claimed in claim 14 further comprising:
a float switch for sensing the quantity of liquid in said flow path which changes state when the quantity of liquid at a particular location within said flow path is below a predetermined amount and said controller being coupled to said float switch.

18. A liquid-circulating thermal therapy system including:

a pad having an inlet tube and an outlet tube which communicate by way of a channel within the pad through which liquid is circulated; and a pump assembly for circulating and heating the liquid, said pump assembly comprising:

a reservoir for the liquid, said reservoir having an inlet and an outlet;

a pump for circulating the liquid when said pump is energized from said outlet of said reservoir to said inlet tube of said pad, through said channel and through said outlet tube of said pad to said inlet of said reservoir to define a flow path through which the liquid circulates, said flow path including said reservoir and said channel;

a heater in thermal contact with said liquid for heating said liquid when said heater is energized;

a temperature sensor in thermal contact with the liquid for sensing the temperature of said liquid; and a self-calibrating controller coupled to said temperature sensor for energizing said heater selectively in dependence upon the temperatue sensed by temperature sensor in order to effect closed-loop control of the temperature of the liquid about a set point temperature; and means for self-calibrating said controller at predetermined time intervals, said means including means for electrically isolating said temperature sensor from said controller while said controller is being self-calibrated.

19. A liquid-circulating thermal therapy system as claimed in claim 18 wherein said predetermined intervals occur sufficiently often to account for changes in the operating environment of said thermal therapy system over the operating cycle of said thermal therapy system.

20. A liquid-circulating thermal therapy system as claimed in claim 19 wherein said predetermined intervals occur about once every eighty (80) seconds.

21. A liquid-circulating thermal therapy system as claimed in claim 19 wherein said predetermined intervals occur no less than once every ten (10) minutes.

* * * * *

UNITED STATES PATENT AND TRADEMARK OFFICE
CERTIFICATE OF CORRECTION

PATENT NO. : 4,844,072
DATED : July 4, 1989
INVENTOR(S) : Ronald L. French; Ronald E. Smith; and Mark J. Buch It is certified that error appears in the above-identified patent and that said Letters Patent is hereby corrected as shown below:

Claim 3, Column 21, Line 17, delete "energy".

Claim 6, Column 21, Line 38, delete "selectably", and insert therefor --selectively--.

Claim 14, Column 22, Line 37, delete "switch".

Claim 16, Column 22, Line 57, delete "elecrically", and insert therefor --electrically--.

Claim 18, Column 23, Line 22, delete "temperatue", and insert therefor --temperature--.

Claim 18, Column 24, Line 1, before "temperature", insert --said--.

Signed and Sealed this

Seventeenth Day of April, 1990

Attest:

HARRY F. MANBECK, JR.

*Attesting Officer*  *Commissioner of Patents and Trademarks*